United States Patent [19]
Samsavar et al.

[11] Patent Number: 5,852,232
[45] Date of Patent: Dec. 22, 1998

[54] ACOUSTIC SENSOR AS PROXIMITY DETECTOR

[75] Inventors: Amin Samsavar, San Jose; Thomas McWaid; Sergey Yudin, both of Fremont, all of Calif.

[73] Assignee: Kla-Tencor Corporation, San Jose, Calif.

[21] Appl. No.: 775,617

[22] Filed: Jan. 2, 1997

[51] Int. Cl.⁶ .............................. G01B 5/28; G01B 17/00
[52] U.S. Cl. ............................................................. 73/105
[58] Field of Search ..................... 73/105, 606; 250/306, 250/307

[56] References Cited

U.S. PATENT DOCUMENTS

| | | |
|---|---|---|
| 4,285,053 | 8/1981 | Kren et al. . |
| 5,319,977 | 6/1994 | Quate et al. ............................... 73/606 |
| 5,528,033 | 6/1996 | Lo et al. . |
| 5,672,816 | 9/1997 | Park et al. ................................. 73/105 |

OTHER PUBLICATIONS

Akamine et al., "Acoustic Microscopy Beyond the Diffraction Limit: An Application of MicroFabrication", IEEE, 1991, pp. 857–859.

Griffith et al. "Dimensional Metrology with Scanning Probe Microscopes", J. Appl. Phys., vol. 74, No. 09, 01 Nov. 1993, pp. R83–R109.

Briggs, Andrew; "An introduction to scanning acoustic microscopy"; *Oxford University Press; Royal Microscopical Society;* 1985.

HS1000 HiSPEED Scanning Acoustic Microscope Brochure; Sonix Inc.; Springfield, Virginia; undated.

"The Application of Scanning Acoustic Microscopy to Control Moisture/Thermal–Induced Package Defects," T.M. Moore et al., *ISTFA Failure Analysis Forum,* 29 Oct.—2 Nov. 1990, pp. 251–258.

*Primary Examiner*—Daniel S. Larkin
*Attorney, Agent, or Firm*—Majestic, Parsons, Siebert & Hsue

[57] ABSTRACT

An acoustic sensor used with a first sensor (such as a profilometer, scanning probe microscope or the like) allows for the positioning of the first sensor with respect to the sample. The acoustic sensor has a greater range than a profilometer or a scanning probe microscope, and a relatively quick response time, which allows it to be an effective proximity detector. Additionally, the acoustic sensor is not affected by the material of the sample's surface layer.

42 Claims, 7 Drawing Sheets

ACOUSTIC SENSOR AS PROXIMITY DETECTOR

BACKGROUND OF THE INVENTION

This invention relates in general to instruments for scanning samples or specimens and, in particular, a system for scanning samples or specimens with improved characteristics.

Profiling instruments were first developed for the purpose of characterizing surfaces in terms of roughness, waviness and form. In recent years, they have been refined for the precise metrology in the measurement and production and control of semiconductor devices. Profiling instruments are also used outside the semiconductor industry, for example, for scanning and sensing optical disks, flat panel displays and other devices.

The sensors commonly used include profilometers, scanning probe microscopes (SPM) or the like. Profilometers have large dynamic range but a fast speed of approach can still result in damage to the probe or the sample upon contact. Scanning probe microscopes on the other hand have a relatively small dynamic range. The small dynamic range greatly limits the speed that the probe can be brought down to sample, or moved from one position on a sample to another. Scanning probe microscopes need to be positioned down on the sample with a relatively slow speed so that the movement of the probe toward the sample can be halted. Otherwise, the probe will crash into the sample, damaging the probe or the sample.

It is desired to have an improved scanning instrument that can allow for better positioning of a sensor, such as a profilometer, scanning probe microscope or the like.

SUMMARY OF THE INVENTION

It is possible to use an optical instrument, such as a laser, to determine the distance that the profilometer, scanning probe microscope or the like is from the sample. This type of system, however, has certain undesirable characteristics. In the semiconductor industry, bare silicon can be very clean and is hard to focus on due to the lack of any features such as particles to focus upon. Additionally, the sample material can vary in reflectivity as a result of the probing wavelength. For example, silicon nitride may be transparent to light at a 650 nanometer wavelength. The surface material or texture of the sample affects the optical response. One possible way around this difficulty is to use a variety of lasers in combination. The disadvantage of this type of system is that it would make the proximity detector undesirably expensive.

The inventors have determined that an acoustic sensor can be advantageously used as a proximity detector for another sensor. The acoustic detector has a larger dynamic range than some sensors, such as profilometers, scanning probe microscopes or the like. Additionally, acoustic sensors have a quick response and can be designed to be surprisingly accurate along the Z-axis. The acoustic sensors can also be made insensitive to lateral variations, such as patterns on the wafer or scratches.

Acoustic sensors are not material dependent like optical sensors. Thus, the sample material could include surface layers of ceramics, metals or semiconductor materials and the response of the acoustic sensor would not be seriously affected by the type of material.

One embodiment of the present invention uses a first sensor along with an acoustic sensor. The first sensor is connected to a positioning means and the system has a controller that is given the acoustic sensor signal to control the position of the first sensor. The first sensor and the acoustic sensor have a known positional relationship.

In another embodiment, the first sensor can be moved towards the sample using information from the acoustic sensor. The first sensor can be moved at a first speed relatively quickly towards the sample. The controller can monitor the distance between the sensors and the sample using the acoustic sensor signal. The speed of approach of the sensors toward the sample can be reduced using this information. This method allows for improved throughput, because the sensors can be moved towards the sample at a greater average speed.

Another inventive method of the present invention is for the acoustic sensor to be used to detect the bow or curve in the sample, and then for the Z-stage to be modified while the sensors or sample are moved in the X–Y direction. In this way, the sensors do not have to move as far from the sample, thus allowing for quick movement from a point A to a point B, and increasing the system throughput.

In another inventive method, the first sensor can have a preferred operating range, and the acoustic sensor can be used to control the positioning of the first sensor such that it is in its preferred operating range. For example, if optical elements are focused upon the sample, the acoustic sensor can be used to maintain the position of the optical elements so that they are in focus upon the sample as the sample or sensors are moved in the X–Y direction.

Additionally, the acoustic sensor can be used by itself in a feedback system. The acoustic sensor can be positioned a certain distance from the sample, a value of the acoustic sensor signal, such as a phase shift or the attenuation, can be determined. Then, as the sensor or sample is moved in the X–Y plane, the acoustic sensor signal value will change as the Z position changes. The feedback system can be designed so that the Z-stage moves to maintain the original distance between the sensor and the sample. This can be done by moving the Z-stage so that a value (phase shift, attenuation) of the acoustic sensor signal remains constant. In this way, a profile of the sample along the X–Y axes can be determined.

DETAILED DESCRIPTION OF THE PREFERRED EMBODIMENT

Figure 1:
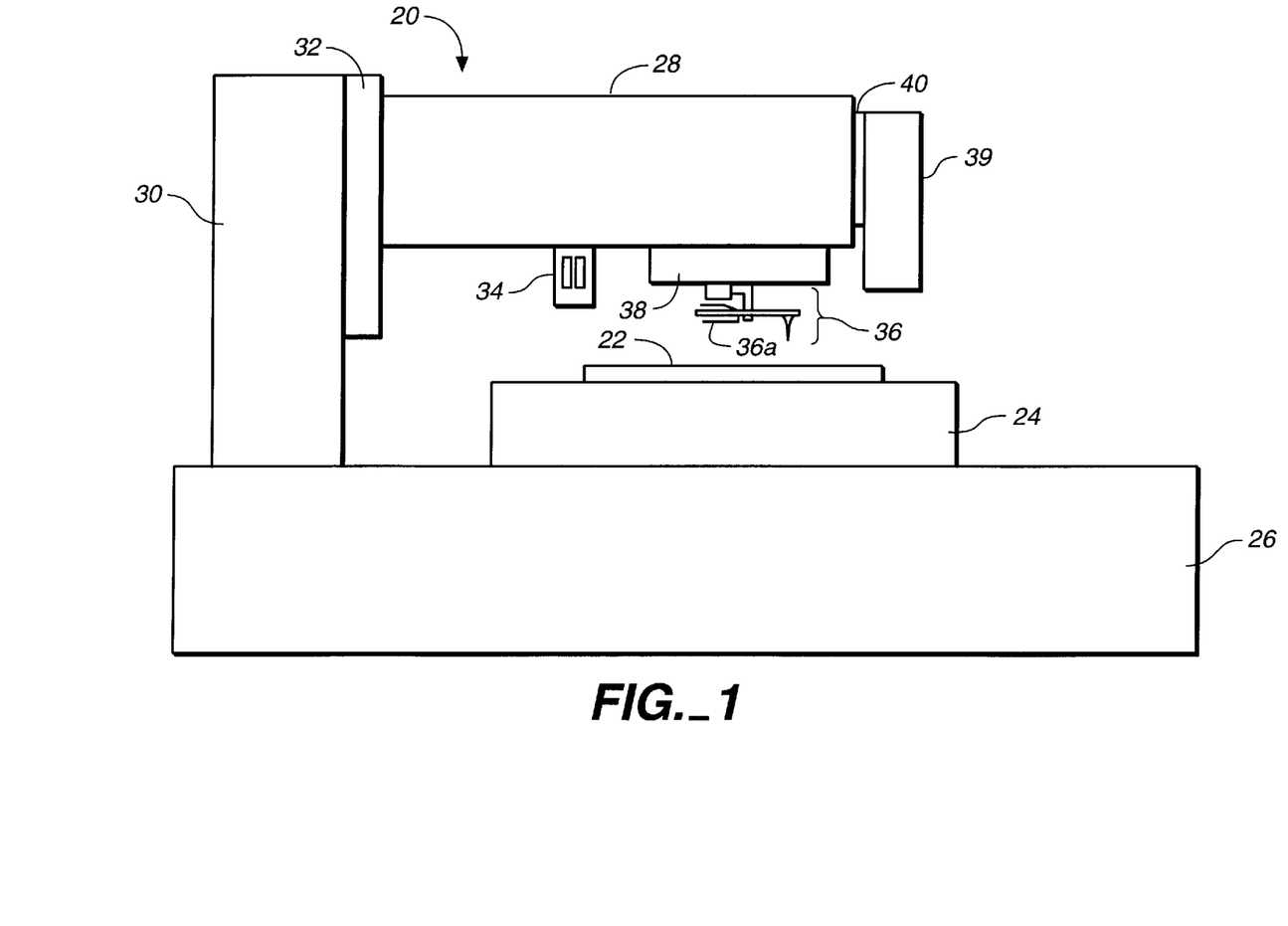
FIG. 1 is a schematic view of an instrument used to illustrate a preferred embodiment of the present invention.

FIG. 1 is a schematic view of an instrument 20 used to illustrate a preferred embodiment of the present invention. The instrument 20 is used for sensing sample 22 and may be a profilometer, for example. The sample 22 is placed on a coarse X–Y stage 24. The coarse X–Y stage 24 moves the sample in its X–Y plane with respect to the sensors. The coarse X–Y stage 24 and the other components of the instrument are supported by the base 26. The sensor head 28 is connected by the Z-stage support 30 to the base 26. The Z-stage elevator 32 moves the sensor head assembly 28 in the Z-axis with respect to the sample 22. The sensor head 28 includes the acoustic sensor 34, which is described in more detail below with respect to FIG. 2. The head assembly 28 also includes the first sensor 36.

In a preferred embodiment, the first sensor 36 is a profilometer including a stylus arm with a stylus tip, a pivot, and a rigid beam. The stylus arm can be connected to a device 36a such as a capacitance gauge, a linear voltage transformer sensor, or a light intensity proximity sensor. Such a pivoted rigid beam profiler is described in the application "Dual Stage Instrument for Scanning a Specimen," Ser. No. 08/598,848 filed Feb. 9, 1996, which is incorporated herein by reference.

The first sensor 36 can also be a scanning probe microscope or the like. The category of scanning probe microscopes includes instruments as diverse as atomic force microscopes and scanning tunneling microscopes. The first sensor may alternately be any other type of sensor.

There is preferably a known positional relationship between the first sensor 36 and the acoustic sensor 34. In a preferred embodiment, the first sensor 36 is positioned on a fine X–Y stage 38. The position of the fine X–Y stage 38 is sent to the controller described below with respect to FIG. 3, and this information can be used to determine the known positional relationship. Alternately, the fine X–Y stage 38 can be moved to a home position which has a known fixed positional relationship between the first sensor 36 and the acoustic sensor 34.

In a preferred embodiment, the acoustic sensor 34 is positioned above the first sensor so that the first sensor can contact or be very close to the sample, while maintaining a separation between the acoustic sensor 34 and the sample 22.

The instrument 20 can also have an optical microscope 39. The optical microscope 39 can have its own Z-stage translator 40.

Figure 2:
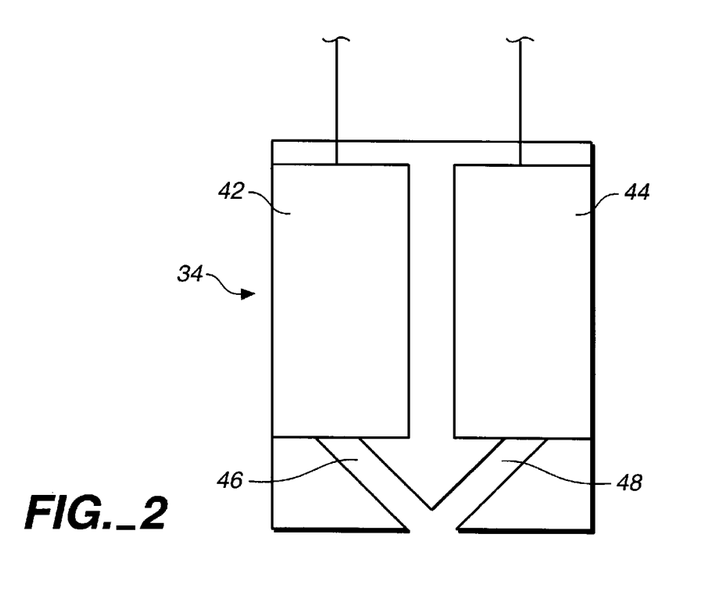
FIG. 2 is a schematic view of an acoustic sensor used with the present invention.

FIG. 2 is a schematic view of an acoustic sensor 34 used with the present invention. The acoustic sensor 34 includes a transmitter 42 and a detector 44. The transmitter 42 and detector 44 can be identical speaker/coil/magnet arrangements. In a preferred embodiment, these transmitters and detectors are SR 7609 available from Knowles located in Itasca, Ill. Alternately, a piezoelectric transducer (PZT) could be used. The transmitter and detector are connected by apertures 46 and 48, respectively. In a preferred embodiment, these apertures are circular tubes having a diameter of about a half-millimeter.

Additionally, in the preferred embodiment, the apertures 46 and 48 are spaced a distance one-and-one-half to two millimeters apart to form an "elephant nose" arrangement. The design of the apertures affects the sensitivity of the acoustic sensor. By bringing the apertures relatively close, the sensitivity of the acoustic sensor along the Z-axis is increased, while the sensitivity for lateral X–Y positions is kept relatively low.

The total width of the acoustic sensor is about five millimeters in a preferred embodiment. In a preferred embodiment, the apertures 46 and 48 are angled in order to keep the spacing between the apertures relatively small.

In a preferred embodiment, the acoustic sensor is operated at a frequency of less than twenty kilohertz. This is much lower than the gigahertz frequencies used in some acoustic microscopes. Additionally, the acoustic sensor of the present invention does not require coupling through a liquid medium such as water. A range of two to ten kilohertz can be used to have the acoustic sensor work in resonant frequency for the system. In the preferred embodiment, a transmitted wave of fifty microwatts at 3.4 kilohertz is used to get a good response curve. In a preferred embodiment, the resolution of the acoustic sensor is ten nanometers along the Z-axis and fifty to one hundred micrometers along the X–Y axes.

Figure 3:
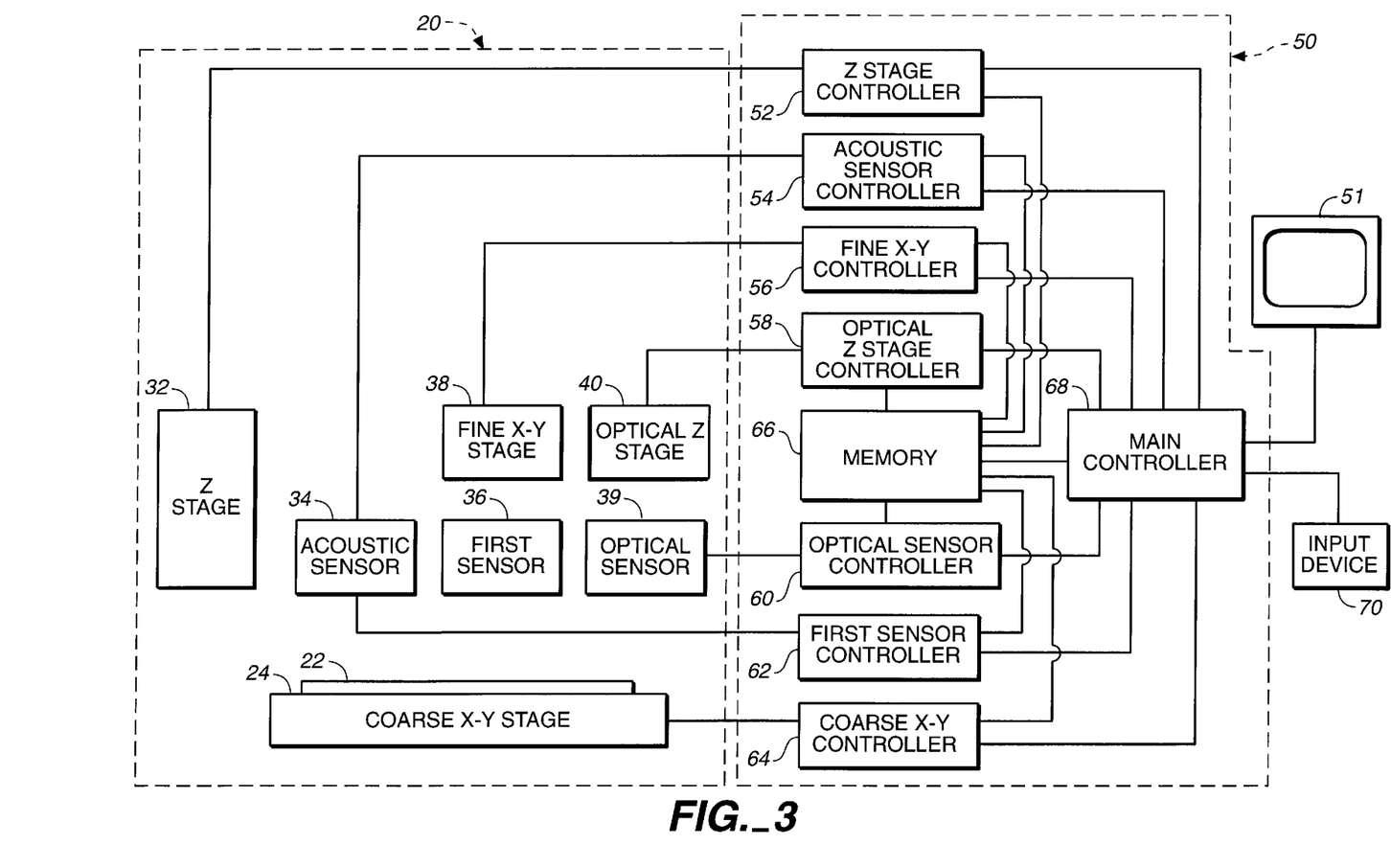
FIG. 3 is a block diagram of the instrument, control and display systems in a preferred embodiment of FIG. 1 of the present invention.

FIG. 3 is a block diagram of the instrument 20, controller 50 and display system 51 of the preferred embodiment. The controller 50 can include multiple controllers 52, 54, 56, 58, 62 and 64 shown in FIG. 3 using a single multi-tasking processor. FIG. 3 shows separate controllers 52, 54, 56, 58, 62 and 64 for the different active elements of the instrument 20. In the embodiment shown, each of the controllers 52–64 are used in memory 66, which they share. This allows for the information such as the acoustic sensor information from acoustic sensor controller 54 to be used to control the positioning means such as the Z-stage 32, coarse X–Y stage 24 and fine X–Y stage 38 or optical Z-stage 40. The different individual controllers are also shown connected to the main controller 68.

The positioning means could be an X–Y stage alone, a Z-stage alone, or any device or combination of devices for positioning the sample with respect to a sensor. Also shown is an input device 70 that can be used for programming the operation of the instrument 20.

Figure 4:
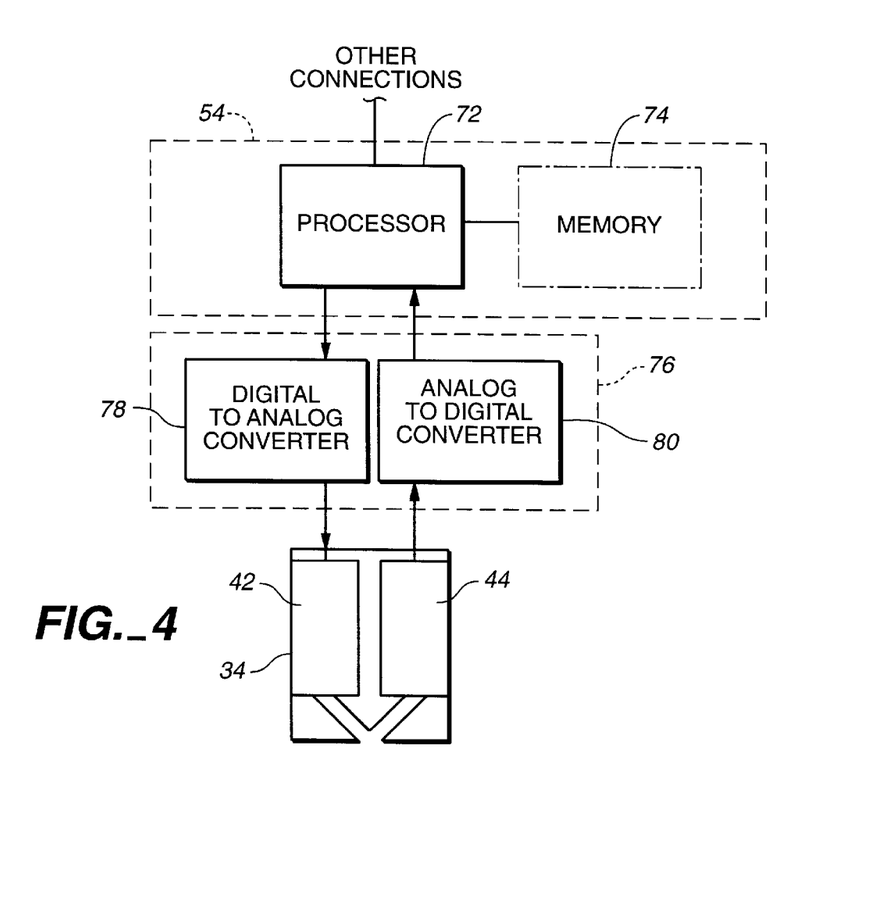
FIG. 4 is a block diagram of an acoustic sensor and controller in a preferred embodiment of the present invention.

FIG. 4 is a block diagram of an acoustic sensor 34 and controller 54. The controller 54 can involve a processor 72 and memory 74. Alternately, a general memory 66 as shown in FIG. 3 could be used. A processor 72 is connected to an interface 76 to convert a digital data in the digital-to-analog converter 78 to an analog signal sent to the transmitter 42 of the acoustic sensor 34. The detector signal is sent in analog form from the detector 44 to the analog-to-digital converter 80, which sends the digital sampled information to the processor 72. The processor 72 can be used to compare the transmitted signal with the received signal. For example, a phase shift of the transmitted signal versus the received signal, the attenuation of the received signal versus the transmitted signal or other waveform changes can be determined. The phase shift between the transmitted and detected signals has been found to be a particularly useful value to determine the distance between the acoustic sensor and the sample.

The controller 54 and digital interface 76 can work in real time because of the relatively low frequencies used for the transmitted acoustic wave; this allows for the quick response of the acoustic sensor system.

Alternately, the circuitry such as that used in the Kren et al. U.S. Pat. No. 4,285,053 entitled "Acoustic Method and Apparatus for Measuring Micron and Submicron Distances," which is incorporated herein by reference, could be used.

Figure 5:
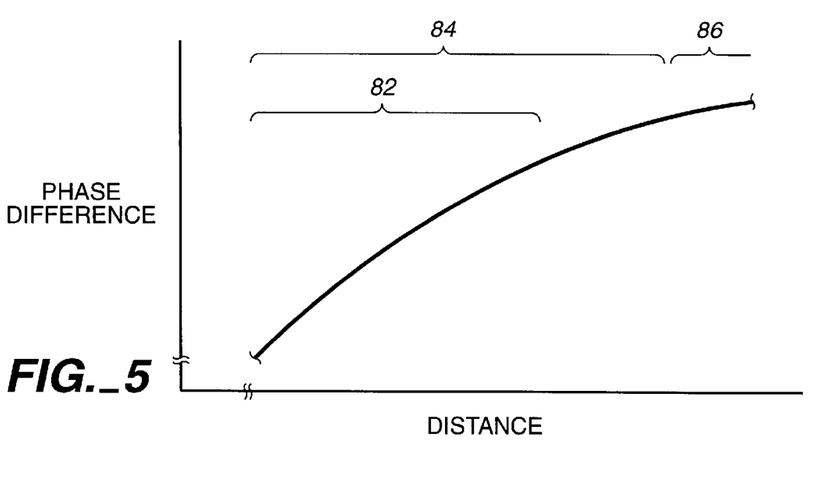
FIG. 5 is a graph illustrating a phase difference versus distance curve.

FIG. 5 is a graph which illustrates a phase difference/ distance relationship. This graph just illustrates the concepts involved, and is not meant to show the exact relationship between phase difference and the distance. As discussed in the Kren et al. patent, there is a range such as range 82 in which the phase difference/distance relationship is relatively linear. There is a larger range, range 84, in which there is a one-to-one relationship between a given phase difference and the distance. At a greater distance, such as in range 86, the accurate determination of a distance for a given phase difference is difficult or impossible, because the curve flattens out. For the transmitted signal frequency and power of the preferred embodiment, the linear region 82 ranges from about zero to 300 microns, the determinable range is from about zero to 500 microns and greater than about 500 microns, the curve flattens out. It is not necessary to rely on the linear relationship between the phase difference and the distance because, as described below, the data can be stored indicating the one-to-one relationship between a phase difference and distance.

Figure 6:
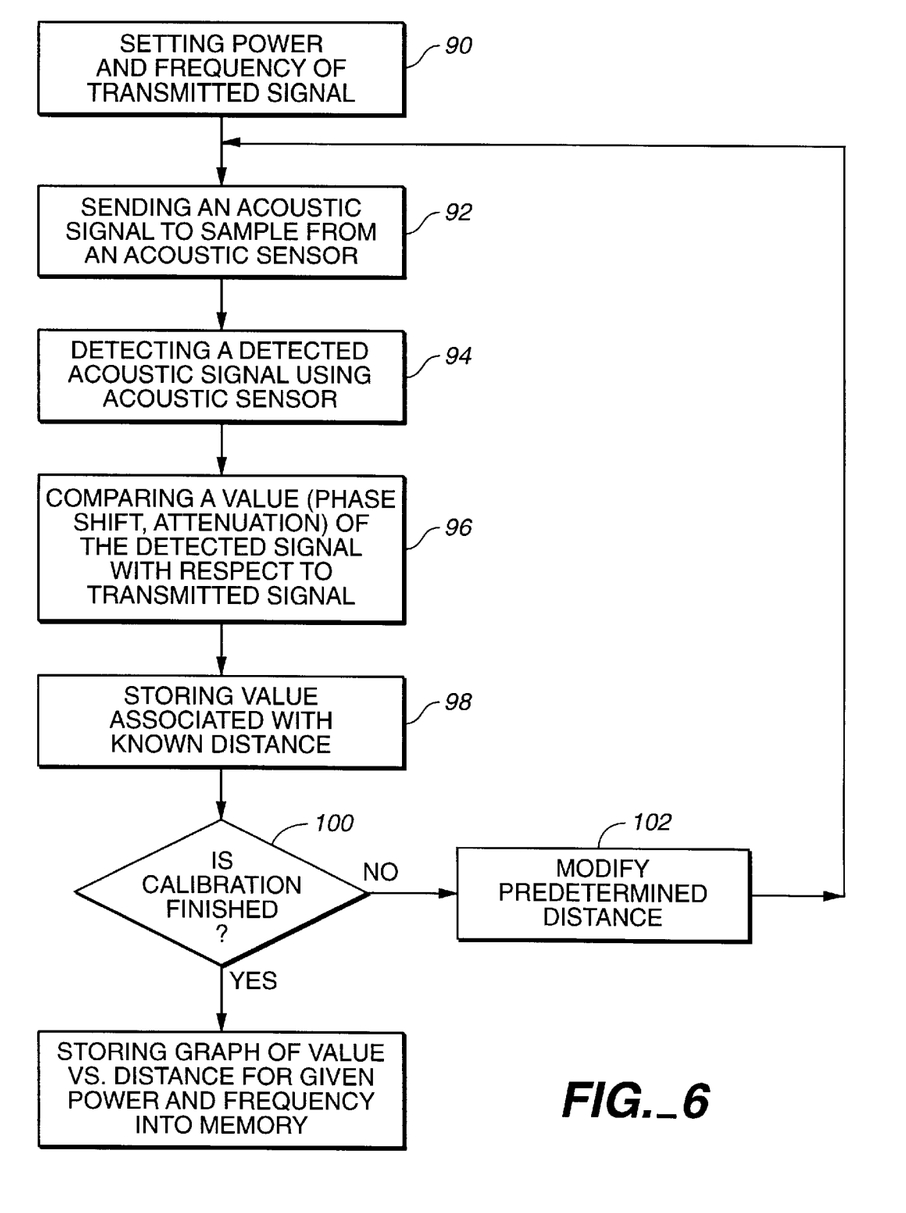
FIG. 6 is a flow chart illustrating the calibration of the preferred embodiment of FIGS. 3 and 4.

FIG. 6 is a calibration method for operating the instrument of FIGS. 3 and 4. In step 90, the power and frequency of the transmitted acoustic signal is set. In step 92, an acoustic signal is sent to the sample from the acoustic sensor. The return signal is detected in step 94. The processor can, in step 96, compare a value of the detected signal with respect to the transmitted signal. This can be, for example, the phase shift or the attenuation or another waveform indication. In step 98, the value associated with the known distance is stored, and in step 100 if the calibration is not finished, the predetermined distance is modified in step 102 and steps 92, 94, 96 and 98 are repeated. When the calibration is finished, a graph of the value, such as the phase shift versus distance for a given power and frequency of transmitted acoustic wave, can be stored into memory. By using the method of FIG. 6, as long as there is one distance value associated with each phase difference, a curve such as that of FIG. 5 can be produced. This curve can be stored in the memory, such as memory 74 of FIG. 4 or memory 66 of FIG. 3.

The calibration method of the present invention can produce an acoustic sensor having the Z-detective sensitivity over the range of zero to 500 microns with a sensitivity of 0.1 microns to 10 microns, preferably one micron. The sensitivity is limited by the noise in the system. In a preferred embodiment, the range is zero to 300 microns with a sensitivity of one micron. The acoustic sensor thus has a wide range compared to a probe and is relatively precise and quick for the reasons discussed above.

Figure 7:
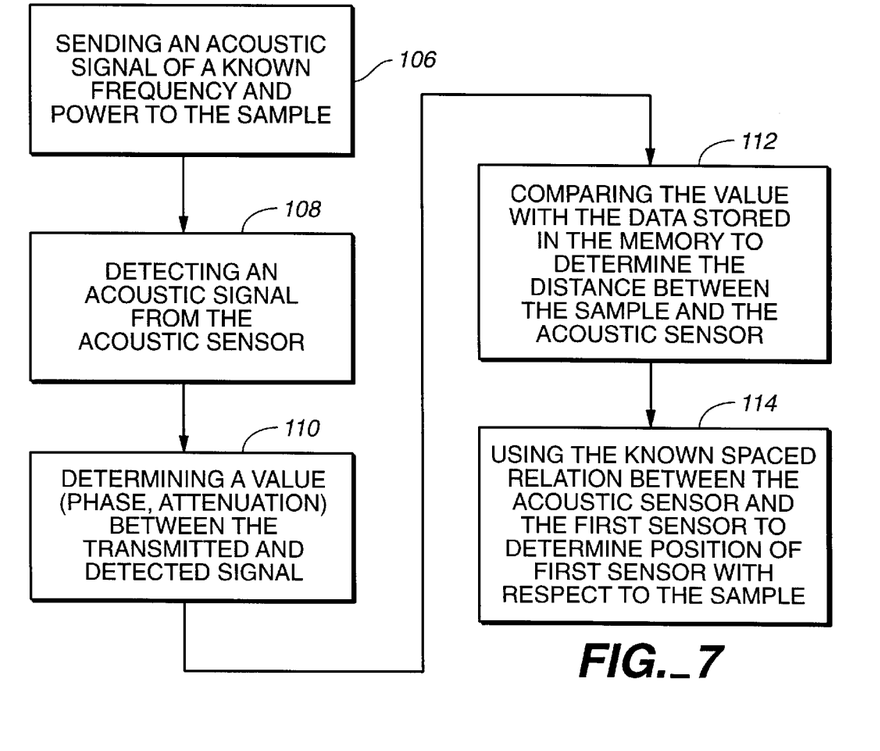
FIG. 7 is a flow chart illustrating the operation of the system of FIGS. 3 and 4.

FIG. 7 shows the operation of an apparatus such as that of FIGS. 3 or 4. In step 106, the acoustic signal of a known frequency and power is sent towards the sample. The return signal is detected in step 108. Next a value, such as phase or attenuation between the transmitted and detected signals, is produced, in step 110. In step 112, this value is compared with the data stored in the memory produced with the calibration method of FIG. 6 to determine the distance between the sample and the acoustic sensor. Optionally, in step 114, the known spatial relation between the acoustic sensor and a first sensor can be used to determine the position of the first sensor with respect to the sample. This information can be used to control the positioning of the sensors with respect to the sample, as described in the inventive methods of FIGS. 8–11.

Figure 8:
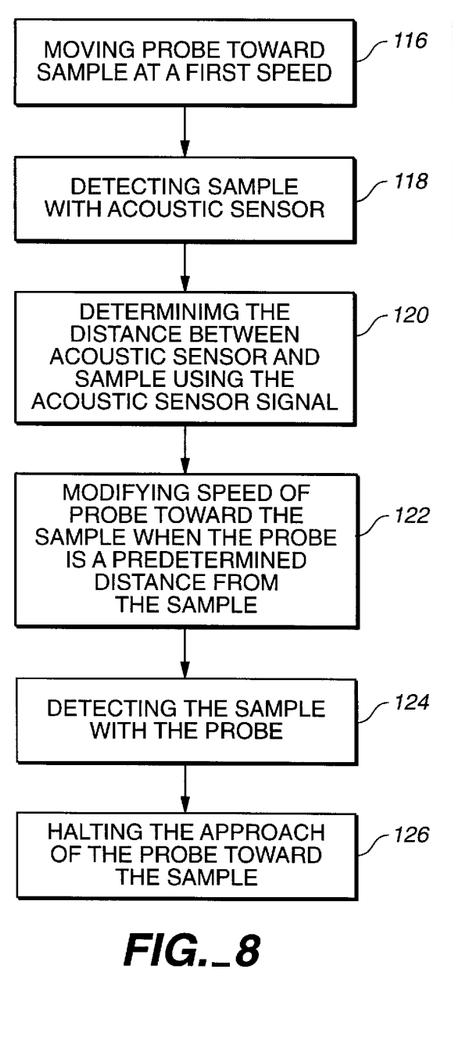
FIG. 8 is a flow chart illustrating an inventive method of using the system to move a probe onto a sample.

FIG. 8 is a flow chart illustrating an inventive method of moving a probe towards the sample. In step 116, the probe is moved towards the sample at a first speed. This first speed can be in the hundreds of microns per second. Because of the small operating range of a probe, if the probe comes down at the sample at hundreds of microns per second, it will be unable to prevent the probe from crashing into the sample. There is only a relatively small period of time available from when the probe first contacts the sample to when the probe crashes into the sample. The greater the speed of the probe; the smaller this period of time. This relatively small period of time is too quick for the probe to sense the sample and tell the positioning means to stop moving the sensor towards the sample. In step 118 of the inventive method, the sample is detected with the acoustic sensor. In Step 120, the distance between the acoustic sensor and the sample is determined using the acoustic sensor sample signal. In step 122, the speed of the probe towards the sample is modified. This can be done when the probe is a predetermined distance from the sample. In a preferred embodiment, the speed can be reduced to one to ten microns per second at a predetermined distance of around fifty microns or less. In step 124, as the sensors move at slower speeds towards the sample, the sample is detected by the probe. Because it is coming in at a slower speed, the probe has more time to respond and, in step 126, halt the approach of the probe towards the sample. Thus, the sensors can be halted before they crash into the sample. Because the sensors can come in at a relatively higher speed at first, the throughput of the device is increased.

Figure 9:
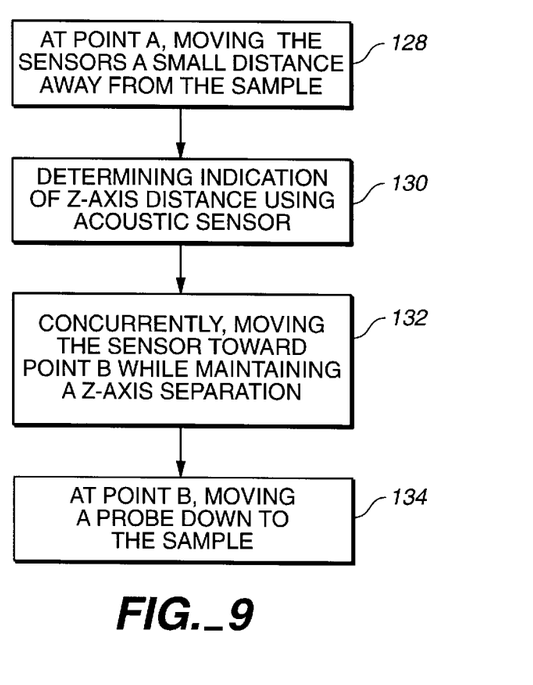
FIG. 9 is a flow chart illustrating an inventive method of moving the probe from point A to point B on the sample.

FIG. 9 is a flow chart illustrating a method of the present invention. In step 128, at point A, the sensors are moved a small distance away from the sample. In step 130, an indication of the Z-axis distance is determined using the acoustic sensor. In step 132, the sensor is moved towards point B, in the X, Y, or θ direction substantially parallel to the surface of the sample, while maintaining a Z-axis separation. The Z-axis separation may be maintained because the acoustic sensor is used to determine the distance between the sensors and the sample. When the sensors reach point B, they can be moved down to this towards the sample in step 134. Because the acoustic sensor has a relatively large range and has a quick response time, it can be used to maintain a Z-axis separation as the sensors move from point A to point B even if the sample has a bow or tilt. For this reason, the sensors do not have to be positioned as high off of the sample in order to avoid problems due to the bow or tilt of a sample. In this way, the throughput of the instrument can be improved when sampling multiple sites across a surface.

Figure 10:
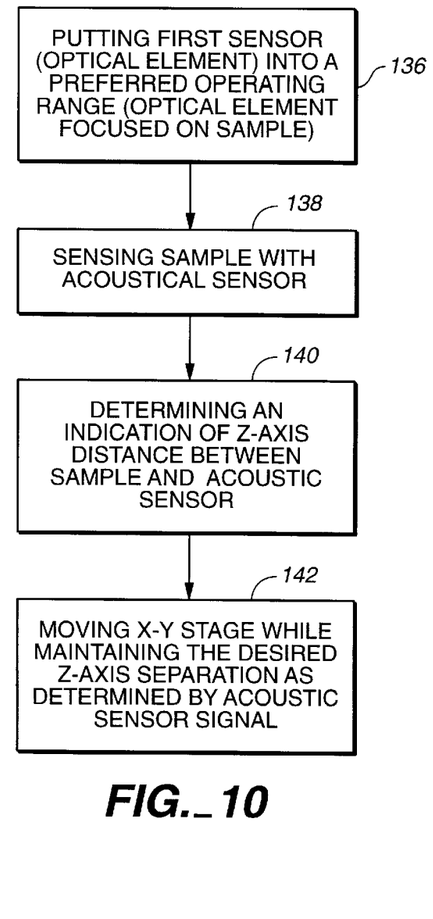
FIG. 10 is a flow chart illustrating an inventive method illustrating keeping a first sensor in a preferred operating mode with the use of information from the acoustic sensor.

FIG. 10 illustrates another inventive method of the present invention. In step 136, a first sensor is put in a preferred operating range. For example, if the first sensor includes an optical element such as an optical microscope, the optical element can be focused upon the sample. In step 138, the sample is sensed with the acoustic sensor. In step 140, an indication of Z-axis distance between the sample and the acoustic sensor is produced. In step 142, the X–Y stage is moved while maintaining the desired Z-axis separation as determined by the acoustic sensor signal.

Figure 11:
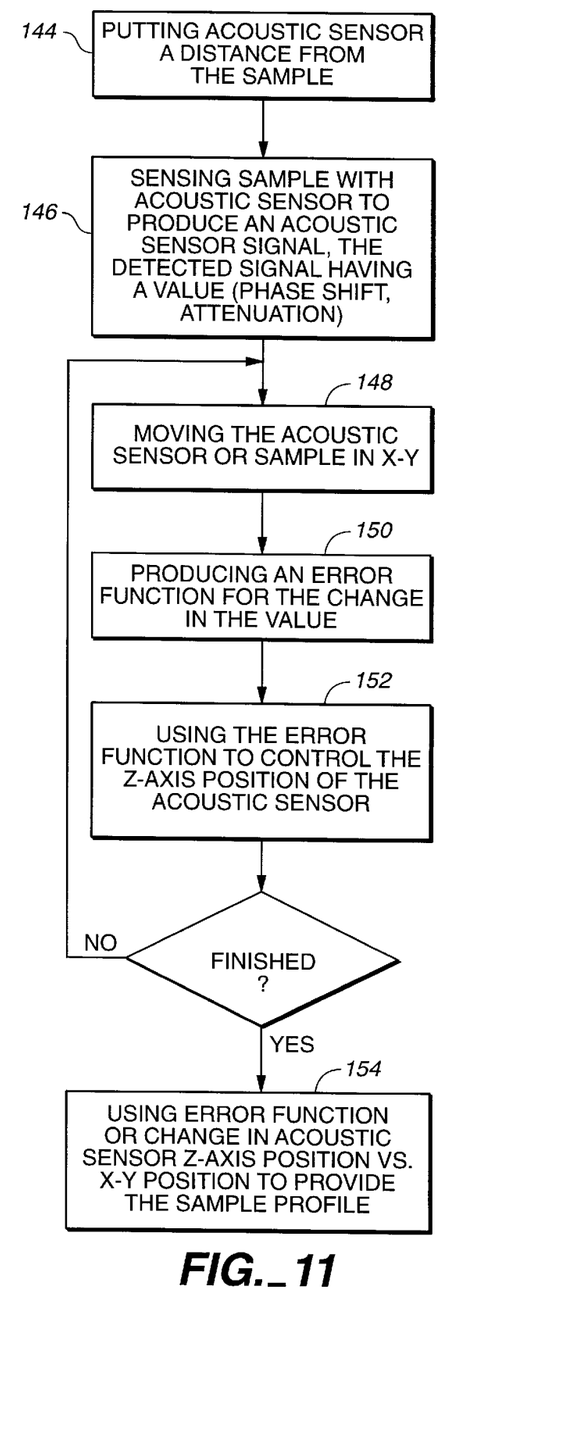
FIG. 11 is a flow chart illustrating an inventive method of using feedback to indicate the profile of the sample using an acoustic sensor signal.

FIG. 11 concerns an inventive method of the present invention using a feedback loop for the controlling the positioning of the acoustic sensor. This method can be used to produce the inventive method of FIG. 10. In step 144, the acoustic sensor is positioned a given distance from the sample set as a reference height. In step 146, the sample is sensed with the acoustic sensor to produce an acoustic sensor signal. The detected signal has a value such as phase shift or attenuation with respect to the transmitted signal. In step 148, the acoustic sensor or sample is moved in the X–Y direction. In step 150, the acoustic sensor signal at height Z is compared to the reference height, the difference between the two provides the error function. In step 152, the error function is used to control the Z-axis position of the acoustic sensor so as to reduce this error function. Thus, as the distance between the sensor and sample increases, the phase difference between the detected and transmitted acoustic signals will increase; and the controller can then cause the Z-axis stage to decrease the separation between the acoustic sensor and the sample. Steps 148, 150 and 152 are repeated as often as necessary. When the operation is finished, the error function or the signal sent to control the Z stage can be used to produce a sample profile, in step 154.

While the invention has been described above with respect to various embodiments, it will be understood that changes and modifications may be made without departing from the scope of the invention, which is to be limited only by the appended claims.

What is claimed is:

1. An instrument for sensing a sample, comprising:
   a first sensor, the first sensor being a profiling device for sensing the sample;
   a separate acoustic sensor having a known positional relation to the first sensor, the acoustic sensor adapted to produce an acoustic sensor signal, the acoustic sensor signal being indicative of the distance from the sample to the acoustic sensor;
   positioning means causing relative motion between the sample and the first sensor; and
   a controller adapted to receive the acoustic sensor signal and control the positioning means.

2. The instrument of claim 1, wherein the controller is adapted to control the positioning means such that the first sensor is positioned within an operating range of the first sensor.

3. The instrument of claim 1, wherein the controller is adapted to control the positioning means to reduce the distance between the sample and the first sensor.

4. The instrument of claim 1 wherein the first sensor comprises a probe adapted to be in contact with the sample.

5. The instrument of claim 4, wherein the first sensor is a profilometer sensor comprising:
   a stylus arm having a stylus tip; and
   a capacitance gauge, a linear voltage differential transformer sensor, or a light intensity proximity sensor operably connected to the stylus arm.

6. The instrument of claim 1 wherein the first sensor comprises a scanning probe microscope.

7. The instrument of claim 6 wherein the first sensor comprises an atomic force microscope.

8. The instrument of claim 1, wherein the first sensor senses thermal variations, or an electrostatic, a magnetic, a light reflectivity, or a light transmission parameter of the sample, or the height variation of a surface of the sample.

9. The instrument of claim 1, wherein the positioning means includes an X–Y translator to hold the sample.

10. The instrument of claim 1, wherein the positioning means includes a Z translator for the first sensor and the acoustic sensor.

11. The instrument of claim 1, wherein the positioning means includes an X–Y translator attached to the first sensor.

12. The instrument of claim 1, wherein the positioning means modifies the position of the first sensor along the Z-axis.

13. The instrument of claim 1, wherein the controller uses the acoustic sensor signal to control the positioning means positioning of the first sensor along the Z-axis.

14. The instrument of claim 1, wherein the first sensor includes an optical element.

15. The instrument of claim 1, wherein the acoustic sensor comprises a transmitter and a detector.

16. The instrument of claim 15, wherein the transmitter is fixed in position with respect to the detector.

17. The instrument of claim 15, wherein the acoustic sensor signal comprises the detected signal from the detector.

18. The instrument of claim 15, wherein the controller is adapted to determine a phase shift between the detected signal and a transmitted signal from the transmitter.

19. The instrument of claim 15, wherein the controller is adapted to determine an amplitude change between the detected signal and a transmitted signal from the transmitter.

20. An instrument for sensing a sample, comprising:
    a first sensor;
    an acoustic sensor having a known positional relation to the first sensor, the acoustic sensor adapted to produce an acoustic sensor signal;
    positioning means causing relative motion between the sample and the first sensor; and
    a controller adapted to receive the acoustic sensor signal and control the positioning means, wherein the controller is adapted to control the positioning means to reduce the distance between the sample and the first sensor, wherein the reduction of the distance between the sample and the first sensor has a rate of speed, wherein the controller is adapted to change this rate of speed.

21. The instrument of claim 20, wherein the controller is adapted to reduce the rate of speed from a first speed to a second speed when the first sensor is a predetermined distance from the sample as indicated by the acoustic sensor signal.

22. The instrument of claim 21, wherein the second speed is less than 10 microns/second.

23. The instrument of claim 21, wherein the predetermined distance is less than 50 microns.

24. An instrument for sensing a sample, comprising:
    a first sensor;
    an acoustic sensor having a known positional relation to the first sensor, the acoustic sensor adapted to produce an acoustic sensor signal;
    positioning means causing relative motion between the sample and the first sensor, the positioning means including an X–Y translator attached to the first sensor; and
    a controller adapted to receive the acoustic sensor signal and control the positioning means, wherein the acoustic sensor is not attached to the X–Y translator.

25. The instrument of claim 24, wherein the X–Y translator has a home position in which the acoustic sensor has a known positional relation to a first sensor.

26. An instrument for sensing a sample, comprising:
    a first sensor, the first sensor including an optical element;
    an acoustic sensor having a known positional relation to the first sensor, the acoustic sensor adapted to produce an acoustic sensor signal;
    positioning means causing relative motion between the sample and the first sensor; and
    a controller adapted to receive the acoustic sensor signal and control the positioning means, wherein the optical element has a focus and wherein the controller uses the acoustic sensor signal to adjust the position of the optical element so that the sample is near the focus of the optical element.

27. An instrument for sensing a sample, comprising:

a first sensor;

an acoustic sensor having a known positional relation to the first sensor, the acoustic sensor adapted to produce an acoustic sensor signal, the acoustic sensor comprising a transmitter and a detector;

positioning means causing relative motion between the sample and the first sensor; and a controller adapted to receive the acoustic sensor signal and control the positioning means, wherein the transmitter produces a transmitted signal having a frequency of less than 20 KHz.

28. A method of operating a sensing instrument comprising:

detecting a sample with an acoustic sensor to produce an acoustic sensor signal;

determining from the acoustic sensor signal the distance between a first sensor and a sample, the first sensor being physically separate from the acoustic sensor and the first sensor being adapted to profile the sample; and adjusting the position of the first sensor with respect to the sample.

29. The method of claim 28, wherein the first sensor has a preferred operating distance range from the sample, wherein the adjusting step is done such that the sample is within the preferred operating range of the first sensor.

30. The method of claim 29, wherein the first sensor is a probe and in the preferred operating distance the probe contacts the sample.

31. The method of claim 28, wherein the first sensor includes an optical element.

32. A method of operating a sensing instrument comprising:

detecting a sample with an acoustic sensor to produce an acoustic sensor signal;

determining from the acoustic sensor signal the distance between a first sensor and a sample; and adjusting the position of the first sensor with respect to the sample, wherein the first sensor includes an optical element and wherein the preferred operating distance is a range where the focus of the optical element is near the sample.

33. A method of operating a sensing instrument comprising:

detecting a sample with an acoustic sensor to produce an acoustic sensor signal;

determining from the acoustic sensor signal the distance between a first sensor and a sample; and adjusting the position of the first sensor with respect to the sample, wherein the first sensor has a preferred operating distance range from the sample, wherein the adjusting step is done such that the sample is within the preferred operating range of the first sensor, wherein the determining and adjusting steps include determining a reference value of the acoustic sensor signal in which the first sensor is within the operating range, and moving the first sensor along the Z-axis so that the acoustic sensor signal matches the reference value.

34. A method of operating a sensing instrument comprising:

detecting a sample with an acoustic sensor to produce an acoustic sensor signal;

determining from the acoustic sensor signal the distance between a first sensor and a sample; and adjusting the position of the first sensor with respect to the sample, wherein the first sensor has a preferred operating distance range from the sample, wherein the adjusting step is done such that the sample is within the preferred operating range of the first sensor, wherein the first sensor is a probe and in the preferred operating distance the probe contacts the sample, further comprising modifying the relative positions of the sample with respect to the acoustic sensor in the X–Y plane while maintaining the first sensor in the operating range.

35. A method of operating a sensing instrument comprising:

moving a first sensor toward a sample at a first speed;

detecting the sample with an acoustic sensor to produce an acoustic sensor signal;

using the acoustic sensor signal to determine the distance between the sample and acoustic sensor; and changing the speed of the first sensor toward the sample.

36. The method of claim 35, wherein the using step comprises determining when the first sensor is a predetermined distance from the sample, and wherein the changing step comprises moving the first sensor toward the sample at a second speed lower than the first speed after the determining step.

37. The method of claim 36, wherein the predetermined distance is less than 50 microns.

38. The method of claim 36, wherein the first speed is greater than 100 microns/second.

39. The method of claim 36, wherein the second speed is less than 10 microns/second.

40. The method of claim 36, wherein the determining step is done by a controller.

41. The method of claim 36, wherein the first sensor produces a signal when the first sensor is near the sample, the second speed being such that the movement of the first sensor can be halted in a manner that the first sensor and the sample are not damaged.

42. The method of claim 35, wherein the first sensor is a probe that contacts a sample.

* * * * *